(12) United States Patent
Walker

(10) Patent No.: US 8,261,376 B1
(45) Date of Patent: Sep. 11, 2012

(54) DEVICE FOR AIDING A PERSON IN URINATION (STRAIGHT SHOOTER)

(76) Inventor: Mort Walker, Stamford, CT (US)

( * ) Notice: Subject to any disclaimer, the term of this patent is extended or adjusted under 35 U.S.C. 154(b) by 0 days.

(21) Appl. No.: 13/366,344

(22) Filed: Feb. 5, 2012

(51) Int. Cl.
*A47K 11/00* (2006.01)
(52) U.S. Cl. .......................................................... 4/144.4
(58) Field of Classification Search .......... 4/144.1–144.4
See application file for complete search history.

(56) References Cited

U.S. PATENT DOCUMENTS

| | | | | |
|---|---|---|---|---|
| 4,796,014 A | * | 1/1989 | Chia | 340/573.5 |
| 5,040,248 A | * | 8/1991 | Kelly | 4/462 |
| 5,566,400 A | * | 10/1996 | Jonec | 4/144.4 |
| 5,722,136 A | * | 3/1998 | Jonec | 4/144.4 |
| 6,081,937 A | | 7/2000 | Whitacre | |
| 6,154,891 A | * | 12/2000 | Wilson | 4/144.4 |
| 6,212,691 B1 | * | 4/2001 | Heberer | 4/144.1 |
| 2002/0002734 A1 | | 1/2002 | Chang | |

* cited by examiner

*Primary Examiner* — Lori Baker
(74) *Attorney, Agent, or Firm* — Richard L. Miller

(57) ABSTRACT

A device that is worn on, and extends only along, the penis of a male user so as to help prevent the male user from misdirecting urine during urination by directing the urine as determined by the male user. The device includes a tube. The tube is worn on, and extends only along, the penis of the male user, and has a working free end. The working free end of the tube is tapered to help aiming and thereby prevent the male user from misdirecting the urine during urination by directing the urine as determined by the male user. In a first embodiment, the device is rigid and reusable, and in a second embodiment, the device is foldable and disposable.

20 Claims, 4 Drawing Sheets

DEVICE FOR AIDING A PERSON IN URINATION (STRAIGHT SHOOTER)

1. BACKGROUND OF THE INVENTION

A. Field of the Invention

The embodiments of the present invention relate to a device for aiding a person in urination, and more particularly, the embodiments of the present invention relate to a reusable or disposable device for wearing on, and extending only along, the penis of a male user so as to help prevent the male user from misdirecting urine during urination by directing the urine as determined by the male user. For example, helping prevent spraying of urine on a stool, the floor, and pants during urination.

B. Description of the Prior Art

Hypospadias is a birth defect of the urethra in the male that involves an abnormally placed urinary meatus—the opening, or male external urethral orifice. Instead of opening at the tip of the glans of the penis, a hypospadic urethra opens anywhere along a line—the urethral groove—running from the tip along the underside—ventral aspect—of the shaft to the junction of the penis and scrotum or perineum.

The urethral meatus opens on the underside of the glans penis in about 50-75% of cases—these are categorized as first degree hypospadias. Second degree—when the urethra opens on the shaft, and third degree—when the urethra opens on the perineum—occur in up to 20 and 30% of cases, respectively.

The more severe degrees are more likely to be associated with chordee, in which the phallus is incompletely separated from the perineum or is still tethered downwards by connective tissue, or with undescended testes—cryptorchidism.

In any event, hypospadias makes it difficult for a male to control the direction of his urine stream. Thus, there exists a need for a reusable or disposable device for wearing on, and extending only along, the penis of a male user so as to help prevent the male user from misdirecting urine during urination by directing the urine as determined by the male user.

Numerous innovations for urine interfacing devices have been provided in the prior art, which will be described below in chronological order to show advancement in the art, and which are incorporated in their entirety herein by reference thereto. Even though these innovations may be suitable for the specific individual purposes to which they address, nevertheless, they differ from the present invention in that they do not teach a reusable or disposable device for wearing on, and extending only along, the penis of a male user so as to help prevent the male user from misdirecting urine during urination by directing the urine as determined by the male user.

(1) U.S. Pat. No. 4,796,014 to Chia

U.S. Pat. No. 4,796,014—issued to Chia on Jan. 3, 1989 in U.S. class 340 and subclass 573.5—teaches a urine-detecting device adapted to be associated with a baby's diaper, which detects and signals the presence of urine after a sufficient time delay from the initiation of urination so as not to interfere with the baby's act of urination. The signal is audio, and optionally, with visual. The device combines sensing apparatus and fastening apparatus, with signalling apparatus attached to it. A fastening apparatus, such as a safety pin with spaced apart electrical conductors on it, is used to engage the device to a diaper. When urine bridges the space between the conductive, a detection circuit is completed, which activates the signal.

(2) U.S. Pat. No. 5,566,400 to Jonec

U.S. Pat. No. 5,566,400—issued to Jonec on Oct. 22, 1996 in U.S. class 4 and subclass 144.4—teaches a disposable male urinary aid that allows a man to urinate directly into a toilet from a standing position by channeling the urine directly into water contained in the toilet bowl. The urinary aid is made of temporarily waterproof paper, and is tapered from a larger diameter at the top end thereof, to a smaller diameter at the bottom end thereof. Following use, the urinary aid may be flushed down the toilet, since it is made entirely of biodegradeable materials. A dispenser is provided to hold, and dispense, a plurality of the urinary aids that are stored in, and dispensed in, a folded, non-interleaved fashion.

(3) U.S. Pat. No. 5,722,136 to Jonec

U.S. Pat. No. 5,722,136—issued to Jonec on Mar. 3, 1998 in U.S. class 4 and subclass 144.4—teaches a disposable male urinary aid that allows a man to urinate directly into a toilet from a standing position by channeling the urine directly into water contained in the toilet bowl. A plurality of the urinary aids are formed as a roll of temporarily waterproof two-ply paper resembling conventional toilet paper, with the roll being divided into sheets by perforations. Multi-sheet segments are divided by double rows of perforations, with each multi-sheet segment forming one of the urinary aids with a channel including a passageway for liquid being formed between the two plies. Following use, the urinary aid may be flushed down the toilet, since it is made entirely of biodegradeable materials.

(4) U.S. Pat. No. 6,081,937 to Whitacre

U.S. Pat. No. 6,081,937—issued to Whitacre on Jul. 4, 2000 in U.S. class 4 and subclass 300.3—teaches an apparatus for absorbing the impact of a stream of liquid entering a body of liquid so as to minimize splash. The apparatus is used within a standard commode bowl to minimize, or eliminate, the amount of splash caused by a stream of urine impacting the body of water contained within the commode bowl. Preferably, the apparatus is capable of floating substantially upon the surface of the body of water within the commode bowl prior to, and during use, and is easily disposable after use by flushing the commode.

(5) United States Patent Application Publication Number 2002/0002734 to Chang United States Patent Application Publication Number 2002/0002734—published to Chang on Jan. 10, 2002 in U.S. class 4 and subclass 144.1—teaches a portable urinal apparatus that includes a supporter attached to the top of a catch basin and a discharge tube attached to the bottom of the catch basin. The catch basin is constructed so as to catch urinary fluids and direct those fluids down through the discharge tube into the toilet bowl of a conventional sit down toilet. An interior chamber is defined by the walls of the catch basin. The sides of the catch basin are sloped to direct fluids towards the middle and bottom of the interior chamber of the catch basin, rather than outside the basin. The bottom of the catch basin is sloped to direct fluids towards the discharge tube. When in use, the bottom end of the discharge tube is positioned over the middle area of the toilet bowl.

It is apparent that numerous innovations for urine interfacing devices have been provided in the prior art, which are adapted to be used. Furthermore, even though these innovations may be suitable for the specific individual purposes to which they address, nevertheless, they would not be suitable for the purposes of the embodiments of the present invention as heretofore described, namely, a reusable or disposable device for wearing on, and extending only along, the penis of a male user so as to help prevent the male user from misdirecting urine during urination by directing the urine as determined by the male user.

2. SUMMARY OF THE INVENTION

Thus, an object of the embodiments of the present invention is to provide a reusable or disposable device for wearing on, and extending only along, the penis of a male user so as to help prevent the male user from misdirecting urine during urination by directing the urine as determined by the male user, which avoids the disadvantages of the prior art.

Briefly stated, another object of the embodiments of the present invention is to provide a device that is worn on, and extends only along, the penis of a male user so as to help prevent the male user from misdirecting urine during urination by directing the urine as determined by the male user. The device includes a tube. The tube is worn on, and extends only along, the penis of the male user, and has a working free end. The working free end of the tube is tapered to help aiming and thereby prevent the male user from misdirecting the urine during urination by directing the urine as determined by the male user. In a first embodiment, the device is rigid and reusable, and in a second embodiment, the device is foldable and disposable.

The novel features considered characteristic of the embodiments of the present invention are set forth in the appended claims. The embodiments of the present invention themselves, however, both as to their construction and to their method of operation together with additional objects and advantages thereof will be best understood from the following description of the specific embodiments when read and understood in connection with the accompanying figures of the drawing.

3. BRIEF DESCRIPTION OF THE FIGURES OF THE DRAWING

The figures of the drawing are briefly described as follows.

4. LIST OF REFERENCE NUMERALS UTILIZED IN THE FIGURES OF THE DRAWING

Figure 1:
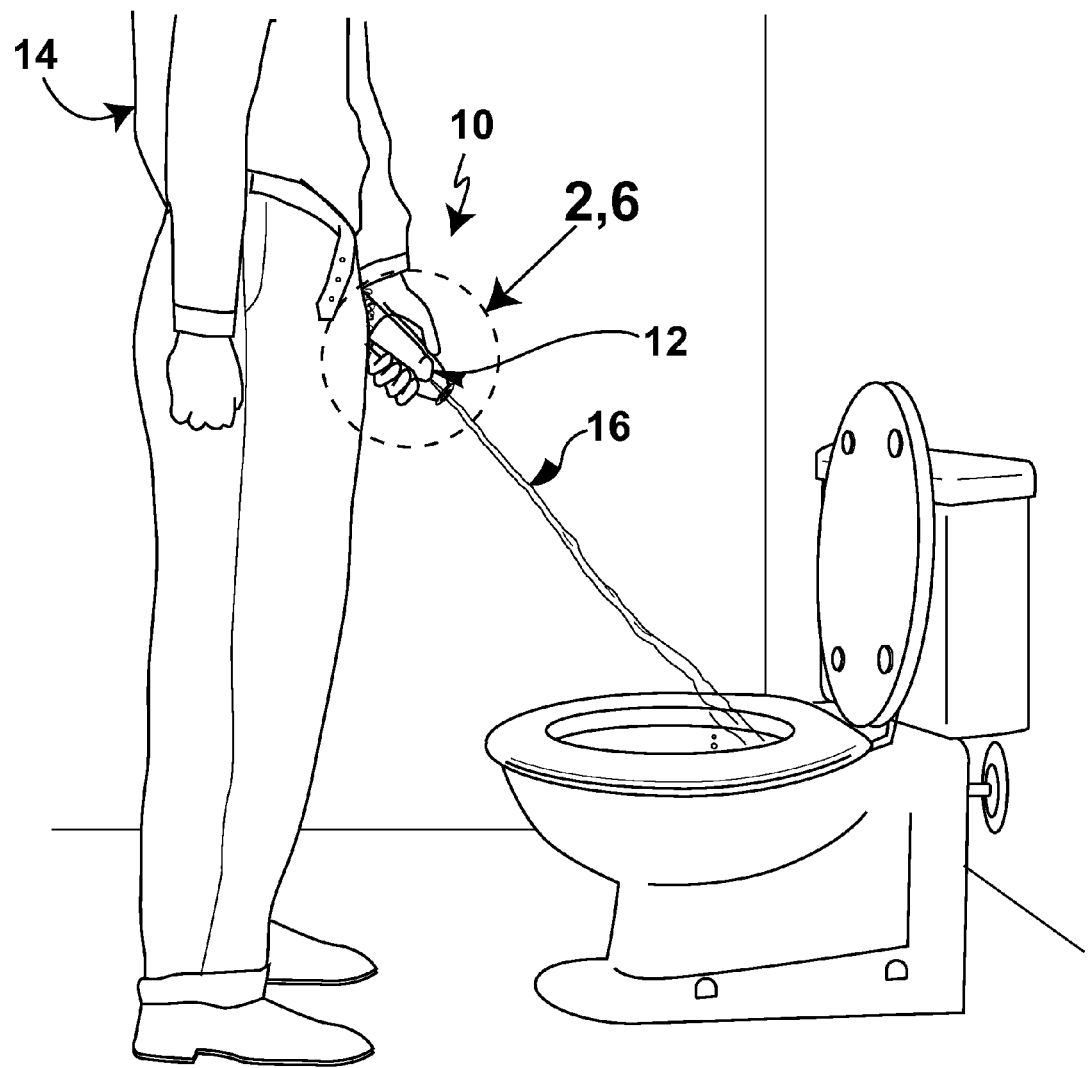
FIG. 1 is a diagrammatic perspective view of the reusable or disposable device of the embodiments of the present invention worn on, and extending only along, the penis of a male user so as to help prevent the male user from misdirecting urine during urination by directing the urine as determined by the male user.

A. Introduction 10 reusable or disposable device of embodiments of present invention for wearing on, and extending only along, penis 12 of male user 14 so as to help prevent male user 14 from misdirecting urine 16 during urination by directing urine 16 as determined by male user 14
12 penis of male user 14
14 male user
16 urine

B. Configuration of Reusable Embodiment of Device 110

110 reusable device
118 tube for wearing on, and extending only along, penis 12 of male user 14
120 working free end of tube 118 for helping prevent male user 14 from misdirecting urine 16 during urination by directing urine 16 as determined by male user 14
122 proximal end of tube 118
124 opening of proximal end 122 of tube 118 for allowing entrance of penis 12 of male user 14 into tube 118
126 opening of working free end 120 of tube 118
128 ring of working free end 120 of tube 118 for providing stop 130
130 stop of ring 128 of working free end 120 of tube 118 for preventing hand of male user 14 from sliding down tube 118 past working free end 120 of tube 118 and into urine 16 streaming out of opening 126 of working free end 120 of tube 118
132 stand
134 base of stand 132 for resting on horizontal surface 136
135 center of base 134 of stand 132
136 horizontal surface
138 hollow post of stand 132
140 distal end of hollow 138 post of stand 132
142 brush of stand 132
144 cover of stand 132
146 controller of stand 132
148 switch of controller 146 of stand 132 for accessing by hand of male user 14
150 arm of controller 146 of stand 132
152 proximal end of arm 150 of controller 146 of stand 132
154 distal end of arm 150 of controller 146 of stand 132
156 hook of distal end 154 of arm 150 of controller 146 of stand 132
158 bore of post 138 of stand 132

C. Configuration of Disposable Embodiment of Device 210

210 disposable device
218 tube for wearing on, and extending only along, penis 12 of male user 14
220 working free end of tube 218
221 pair of axial fold lines of tube 218
222 proximal end of tube 218
224 opening of proximal end 222 of tube 218 for allowing entrance of penis 12 of male user 14 into tube 218
226 opening of working free end 220 of tube 218
260 biodegradable foldable material of tube 218

262 waterproof layer of tube 218 for preventing urine 16 from passing through biodegradable foldable material 260 of tube 218 and onto hand of male user 14

5. DETAILED DESCRIPTION OF THE PREFERRED EMBODIMENTS

A. Introduction

Referring now to the figures, in which like numerals indicate like parts, and particularly to FIG. 1, which is a diagrammatic perspective view of the reusable or disposable device of the embodiments of the present invention worn on, and extending only along, the penis of a male user so as to help prevent the male user from misdirecting urine during urination by directing the urine as determined by the male user, the reusable or disposable device of the embodiments of the present invention is shown generally at 10 for wearing on, and extending only along, the penis 12 of a male user 14 so as to help prevent the male user 14 from misdirecting urine 16 during urination by directing the urine 16 as determined by the male user 14.

B. Configuration of a Reusable Embodiment of the Device 110

Figure 2:
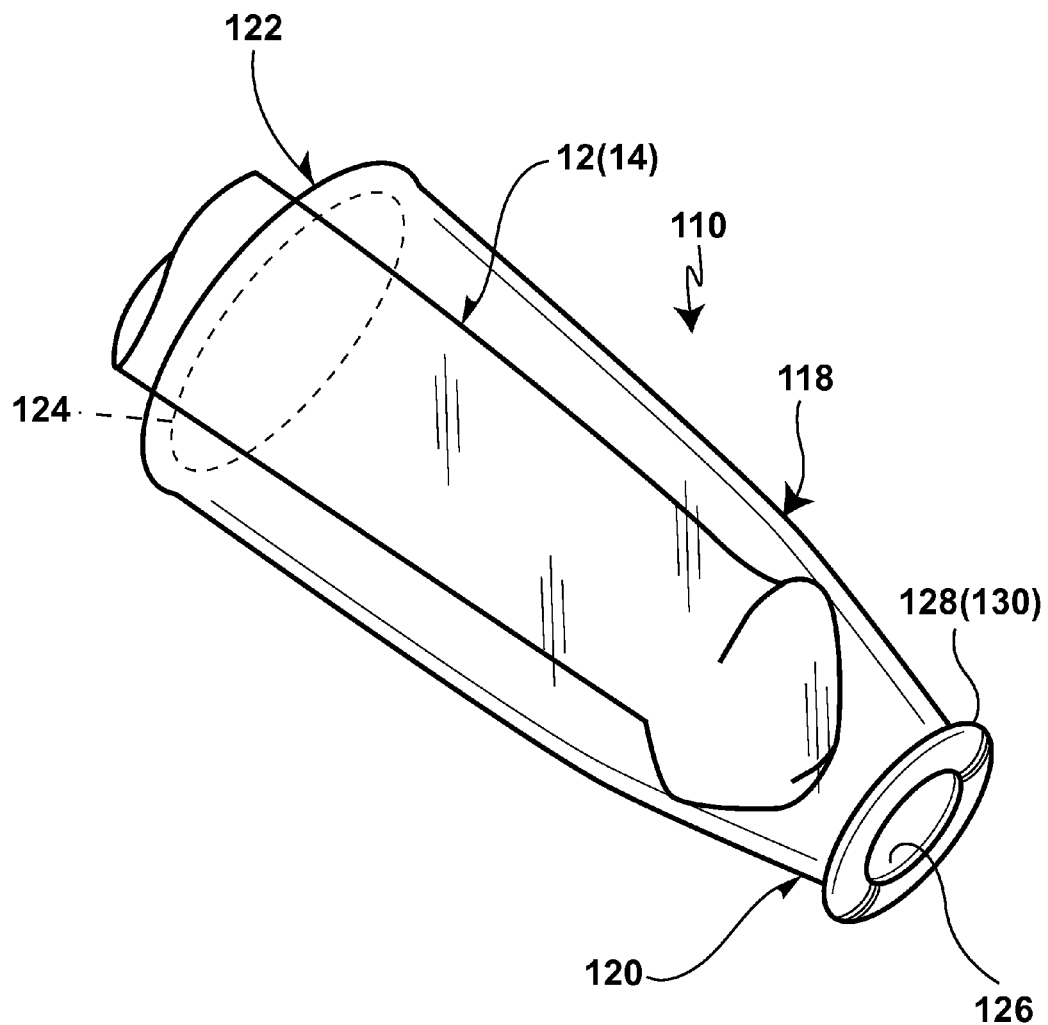
FIG. 2 is an enlarged diagrammatic perspective view of the area generally enclosed by the dotted curve identified by ARROW 2 in FIG. 1 of a resusable embodiment of the present invention.
Figure 3:
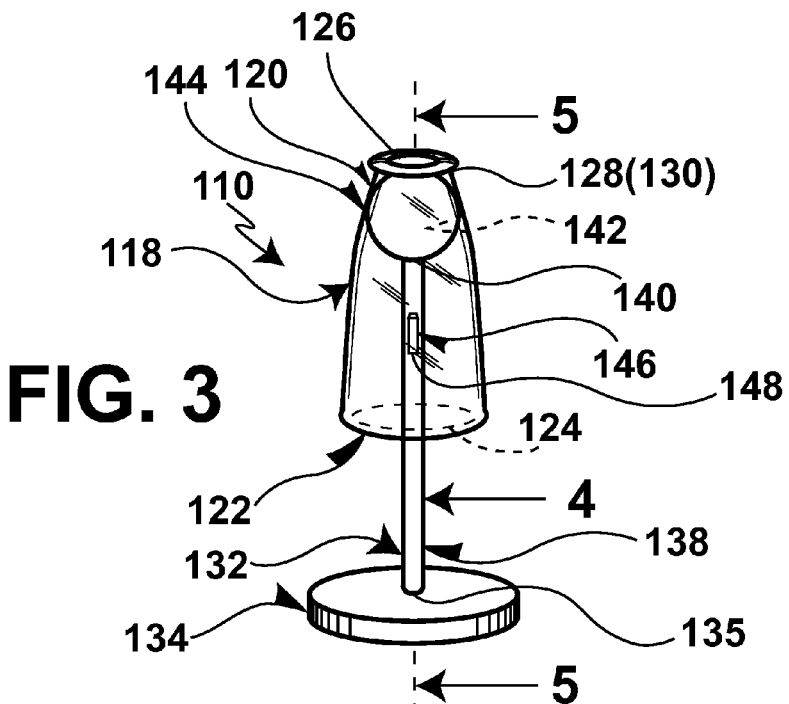
FIG. 3 is a reduced diagrammatic perspective view of the reusable device of the present invention shown in FIG. 2 in combination with a stand.

The configuration of a reusable embodiment of the device 110 can best be seen in FIGS. 2-5, which are, respectively, an enlarged diagrammatic perspective view of the area generally enclosed by the dotted curve identified by ARROW 2 in FIG. 1 of a reusable embodiment of the present invention, a reduced diagrammatic perspective view of the reusable device of the present invention shown in FIG. 2 in combination with a stand, an enlarged diagrammatic side elevational view of the stand identified by ARROW 4 in FIG. 3, and an enlarged diagrammatic cross sectional view taken along LINE 5-5 in FIG. 3, and as such, will be discussed with reference thereto.

The reusable device 110 comprises a tube 118.

The tube 118 is for wearing on, and extending only along, the penis 12 of the male user 14, and has a working free end 120.

The working free end 120 of the tube 118 is tapered for helping aiming and thereby prevent the male user 14 from misdirecting the urine 16 during urination by directing the urine 16 as determined by the male user 14.

The tube 118 is made of rigid plastic so as to be washable, and thereby reusable.

The tube 118 further has a proximal end 122. The proximal end 122 of the tube 118 has an opening 124. The opening 124 of the proximal end 122 of the tube 118 is for allowing entrance of the penis 12 of the male user 14 into the tube 118.

The working free end 120 of the tube 118 has an opening 126.

The opening 126 of the working free end 120 of the tube 118 is smaller than the opening 124 of the proximal end 122 of the tube 118.

The proximal end 122 of the tube 118 is bullnosed for comfort against the pelvic area of the male user 14 during use of the reusable device 110.

The working free end 120 of the tube 118 has a ring 128.

The ring 128 of the working free end 120 of the tube 118 extends therearound, and is for providing a stop 130 for preventing the hand of the male user 14 from sliding down the tube 118 past the working free end 120 of the tube 118 and into the urine 16 streaming out of the opening 126 of the working free end 120 of the tube 118.

Figures 4, 5:
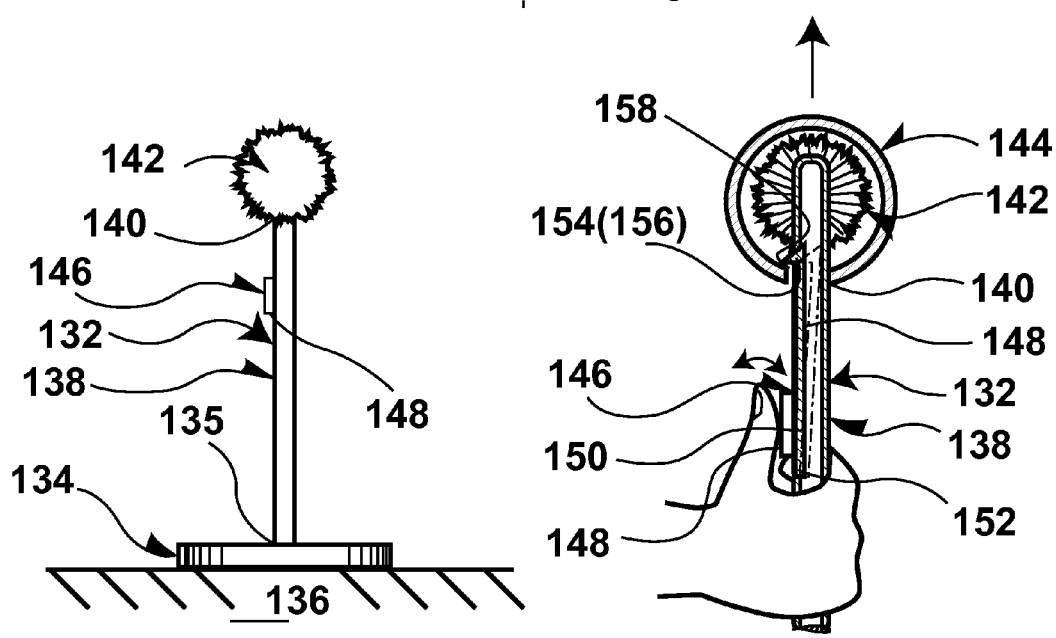
FIG. 4 is an enlarged diagrammatic side elevational view of the stand identified by ARROW 4 in FIG. 3.
FIG. 5 is an enlarged diagrammatic cross sectional view taken along LINE 5-5 in FIG. 3.

As shown in FIGS. 3-5, the reusable device 110 further comprises a stand 132.

The stand 132 supports the tube 118 vertically when not in use.

The stand 132 has a base 134.

The base 134 of the stand 132 has a center 135, and is for resting on a horizontal surface 136.

The stand 132 further has a hollow post 138.

The hollow post 138 of the stand 132 extends vertically upwardly from the center 135 of the base 134 of the stand 132, and terminates in a distal end 140.

The stand 132 further has a brush 142.

The brush 142 of the stand 132 is disposed on the distal end 140 of the hollow post 138 of the stand 132, and is used to clean the tube 118.

The brush 142 of the stand 132 is generally spherical.

The stand 132 further has a cover 144.

The cover 144 of the stand 132 replaceably encompasses, and protects, the brush 142 of the stand 132 when the stand is supporting the tube 118, and when removed, allows the brush 142 of the stand 132 to clean the tube 118.

The cover 144 of the stand 132 is generally spherical so as to hide the brush 142 of the stand 132 therein when the stand 132 is being used to support the tube 118.

The stand 132 further has a controller 146.

The controller 146 comprises a switch 148 and an arm 150.

The switch 148 of the controller 146 of the stand 132 is pivotally mounted to the hollow post 138 of the stand 132, and is for accessing by the hand of the male user 14.

The arm 150 of the controller 146 of the stand 132 is disposed within the hollow post 138 of the stand 132, and has a proximal end 152 and a distal end 154.

The proximal end 152 of the arm 150 of the controller 146 of the stand 132 is operatively connected to the switch 148 of the controller 146 of the stand 132.

The distal end 154 of the arm 150 of the controller 146 of the stand 132 has a hook 156 thereat.

The hook 156 of the distal end 154 of the arm 150 of the controller 146 of the stand 132 moves in and out of a bore 158 in the post 138 of the stand 132, and when the hook 156 of the distal end 154 of the arm 150 of the controller 146 of the stand 132 normally passes through the bore 158 in the post 138 of the stand 132, the hook 156 of the distal end 154 of the arm 150 of the controller 146 of the stand 132 engages in the cover 144 of the stand 132, thereby preventing removal of the cover 144 of the stand 132, and when the switch 148 of the controller 146 of the stand 132 is pressed in, the arm 150 of the controller 146 of the stand 132 is pivoted inwardly, thereby disengaging the hook 156 of the distal end 154 of the arm 150 of the controller 146 of the stand 132 from the cover 144 of the stand 132, and thereby allow the cover 144 of the stand 132 to be removed to expose the brush 142 of the stand 132.

C. Configuration of a Disposable Embodiment of the Device 210

Figure 6:
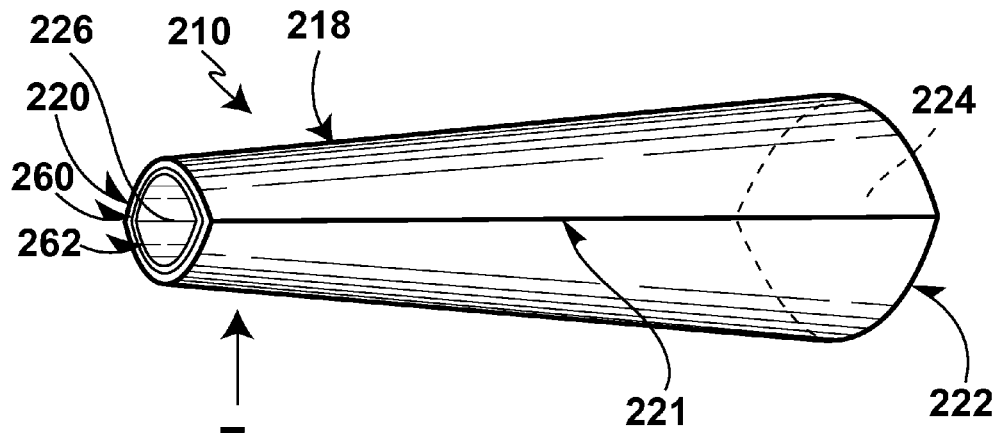
FIG. 6 is an enlarged diagrammatic perspective view of the area generally enclosed by the dotted curve identified by ARROW 6 in FIG. 1 of a disposable embodiment of the present invention.
Figure 7:
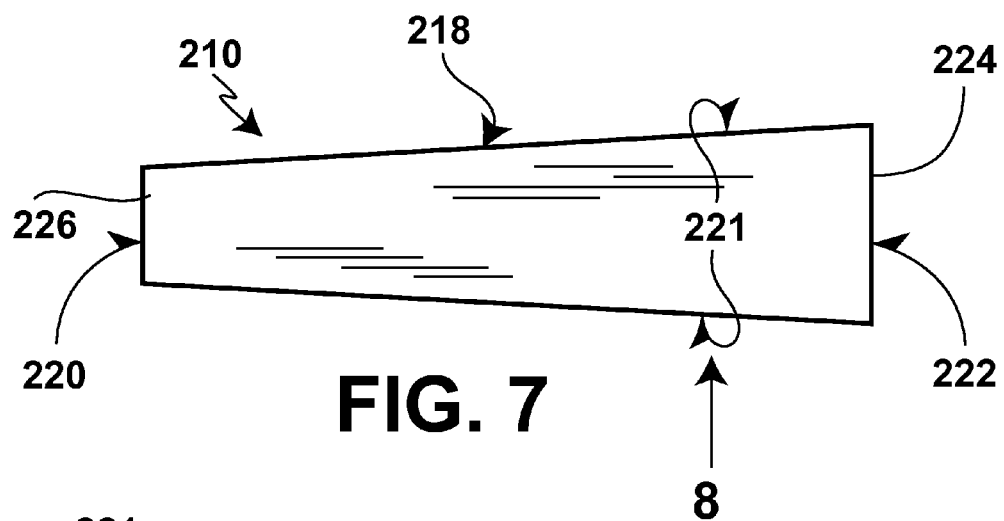
FIG. 7 is a diagrammatic bottom plan view taken generally in the direction of ARROW 7 in FIG. 6 of the disposable embodiment of the present invention collapsed.
Figure 8:
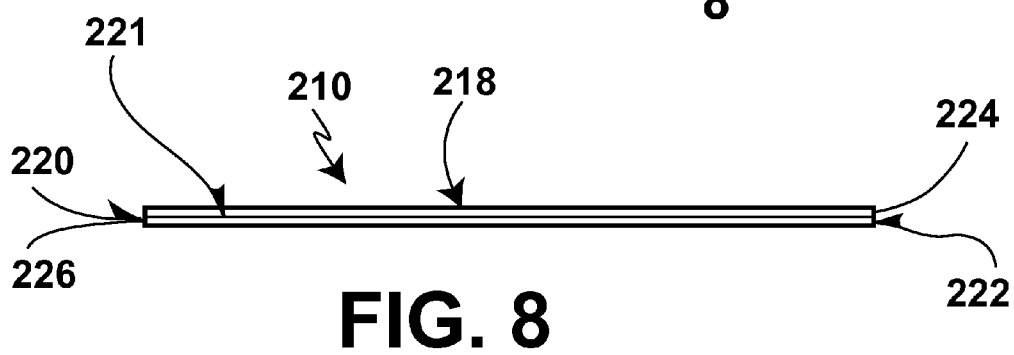
FIG. 8 is a diagrammatic side elevational view taken in the direction of ARROW 8 in FIG. 7.

The configuration of a disposable embodiment of the device 210 can best be seen in FIGS. 6-8, which are, respectively, an enlarged diagrammatic perspective view of the area generally enclosed by the dotted curve identified by ARROW 6 in FIG. 1 of a disposable embodiment of the present invention, a diagrammatic bottom plan view taken generally in the direction of ARROW 7 in FIG. 6 of the disposable embodiment of the present invention collapsed, and a diagrammatic side elevational view taken in the direction of ARROW 8 in FIG. 7, and as such, will be discussed with reference thereto.

The disposable device 210 comprises a tube 218.

The tube 218 is for wearing on, and extending only along, the penis 12 of the male user 14, and has a working free end 220.

The working free end 220 of the tube 218 is tapered for helping aiming and thereby prevent the male user 14 from misdirecting the urine 16 during urination by directing the urine 16 as determined by the male user 14.

The tube 218 is disposable, and foldable from an in-use mode (FIG. 6) to a collapsed mode (FIGS. 7 and 8).

In the in-use mode, the tube 218 is truncated cone-shaped, and in the collapsed mold, the tube 218 is folded on a pair of axial fold lines 221 of the tube 218 flat to be trapezoidal-shaped.

The tube 218 further has a proximal end 222. The proximal end 222 of the tube 218 has an opening 224. The opening 224 of the proximal end 222 of the tube 218 is for allowing entrance of the penis 12 of the male user 14 into the tube 218.

The working free end 220 of the tube 218 has an opening 226.

The opening 226 of the working free end 220 of the tube 218 is smaller than the opening 224 of the proximal end 222 of the tube 218.

The tube 218 is made of a biodegradable foldable material 260 so as to be foldable and flushably disposable, and is lined with a waterproof layer 262. The waterproof layer 262 of the tube 218 is for preventing the urine 16 from passing through the biodegradable foldable material 260 of the tube 218 and onto the hand of the male user 14 during use of the disposable device 210.

D. Impressions

It will be understood that each of the elements described above or two or more together may also find a useful application in other types of constructions differing from the types described above.

While the embodiments of the present invention have been illustrated and described as embodied in a reusable or disposable device for wearing on, and extending only along, the penis of a male user so as to help prevent the male user from misdirecting urine during urination by directing the urine as determined by the male user, however, they are not limited to the details shown, since it will be understood that various omissions, modifications, substitutions, and changes in the forms and details of the embodiments of the present invention illustrated and their operation can be made by those skilled in the art without departing in any way from the spirit of the embodiments of the present invention.

Without further analysis, the foregoing will so fully reveal the gist of the embodiments of the present invention that others can by applying current knowledge readily adapt them for various applications without omitting features that from the standpoint of prior art fairly constitute characteristics of the generic or specific aspects of the embodiments of the present invention.

The invention claimed is:

1. A reusable device for wearing on, and extending only along, the penis of a male user so as to help prevent the male user from misdirecting urine during urination by directing the urine as determined by the male user, comprising:
a tube;
wherein said tube is for wearing on, and extending only along, the penis of the male user;
wherein said tube has a working free end;
wherein said working free end of said tube is tapered for helping aiming and thereby prevent the male user from misdirecting the urine during urination by directing the urine as determined by the male user;
further comprising a stand;
wherein said stand has a base;
wherein said base of said stand is for resting on a horizontal surface;
wherein said stand has a hollow post, wherein said base of said stand has a center;
wherein said hollow post of said stand extends vertically upwardly from said center of said base of said stand; and
wherein said hollow post of said stand terminates in a distal end.

2. The reusable device of claim 1, wherein said tube has a proximal end;
wherein said proximal end of said tube has an opening; and
wherein said opening of said proximal end of said tube is for allowing entrance of the penis of the male user into said tube.

3. The reusable device of claim 2, wherein said working free end of said tube has an opening; and
wherein said opening of said working free end of said tube is smaller than said opening of said proximal end of said tube.

4. The reusable device of claim 2, wherein said proximal end of said tube is bullnosed for comfort against the pelvic area of the male user during use of said reusable device.

5. The reusable device of claim 3, wherein said working free end of said tube has a ring;
wherein said ring of said working free end of said tube extends therearound; and
wherein said ring of said working free end of said tube is for providing a stop for preventing the hand of the male user from sliding down said tube past said working free end of said tube and into the urine streaming out of said opening of said working free end of said tube during use of said reusable device.

6. The reusable device of claim 1, wherein said tube is made of rigid plastic so as to be washable, and thereby reusable.

7. The reusable device of claim 1, wherein said stand has a brush.

8. The reusable device of claim 7, wherein said brush of said stand is disposed on said distal end of said hollow post of said stand; and
wherein said brush of said stand is used to clean said tube.

9. The reusable device of claim 7, wherein said brush of said stand is generally spherical.

10. The reusable device of claim 7, wherein said stand has a cover.

11. The reusable device of claim 10, wherein said cover of said stand replaceably encompasses, and protects, said brush of said stand when said stand is supporting said tube, and when removed, allows said brush of said stand to clean said tube.

12. The reusable device of claim 10, wherein said cover of said stand is generally spherical so as to hide said brush of said stand therein when said stand is being used to support said tube.

13. The reusable device of claim 10, wherein said stand has a controller.

14. The reusable device of claim 13, wherein said controller comprises a switch.

15. The reusable device of claim 14, wherein said switch of said controller of said stand is pivotally mounted to said hollow post of said stand; and
wherein said switch of said controller of said stand is for accessing by the hand of the male user.

16. The reusable device of claim 14, wherein said controller comprises an arm.

17. The reusable device of claim 15, wherein said arm of said controller of said stand is disposed within said hollow post of said stand.

18. The reusable device of claim 16, wherein said arm of said controller of said stand has a proximal end; and wherein said proximal end of said arm of said controller of said stand is operatively connected to said switch of said controller of said stand.

19. The reusable device of claim 16, wherein said arm of said controller of said stand has a distal end; and wherein said distal end of said arm of said controller of said stand has a hook.

20. The reusable device of claim 19, wherein said hook of said distal end of said arm of said controller of said stand moves in and out of a bore in said hollow post of said stand, and when said hook of said distal end of said arm of said controller of said stand normally passes through said bore in said hollow post of said stand, said hook of said distal end of said arm of said controller of said stand engages in said cover of said stand, thereby preventing removal of said cover of said stand, and when said switch of said controller of said stand is pressed in, said arm of said controller of said stand is pivoted inwardly, thereby disengaging said hook of said distal end of said arm of said controller of said stand from said cover of said stand, and thereby allow said cover of said stand to be removed to expose said brush of said stand.

* * * * *